(12) United States Patent
Kiso

(10) Patent No.: US 8,344,002 B2
(45) Date of Patent: Jan. 1, 2013

(54) COMPOUND HAVING β-SECRETASE INHIBITORY ACTIVITY

(76) Inventor: Yoshiaki Kiso, Ibaraki (JP)

( * ) Notice: Subject to any disclaimer, the term of this patent is extended or adjusted under 35 U.S.C. 154(b) by 396 days.

(21) Appl. No.: 12/452,234

(22) PCT Filed: Jun. 18, 2008

(86) PCT No.: PCT/JP2008/061141
§ 371 (c)(1),
(2), (4) Date: Dec. 22, 2009

(87) PCT Pub. No.: WO2009/001730
PCT Pub. Date: Dec. 31, 2008

(65) Prior Publication Data
US 2010/0137606 A1 Jun. 3, 2010

(30) Foreign Application Priority Data
Jun. 22, 2007 (JP) ................. 2007-164845

(51) Int. Cl.
| A61K 31/4412 | (2006.01) |
| A61K 31/4525 | (2006.01) |
| A61K 31/454 | (2006.01) |
| A61K 31/421 | (2006.01) |
| A61K 31/41 | (2006.01) |
| C07D 263/06 | (2006.01) |
| C07D 257/04 | (2006.01) |
| C07D 401/12 | (2006.01) |
| C07D 413/14 | (2006.01) |
| C07D 213/40 | (2006.01) |

(52) U.S. Cl. ........ 514/340; 514/374; 514/381; 514/382; 546/268.4; 546/271.4; 546/323; 548/215; 548/253

(58) Field of Classification Search .................. None
See application file for complete search history.

(56) References Cited

U.S. PATENT DOCUMENTS
2007/0004637 A1   1/2007   Kiso
2009/0198056 A1   8/2009   Mimoto et al.

FOREIGN PATENT DOCUMENTS
| WO | 01/00665 | 1/2001 |
| WO | 2004/076478 | 9/2004 |
| WO | 2007/029587 | 3/2007 |

OTHER PUBLICATIONS

Ettmayer et al. "Lessons Learned from Marketed and Investigational Prodrugs." J. Med. Chem., (2004), 47(10): 2393-2404.*
Hamada et al. Bioorg. Med. Chem. Lett. 18 (2008), pp. 1654-1658.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Wolff et al. Burger's Medicinal Chemistry and Drug Discovery. 5th ed. vol. 1: Principles and Practice (1995). pp. 975-977.*
Stachel et al. J. Med. Chem. 2004, 47, pp. 6447-6450.*

Supplementary European Search Report dated Jun. 28, 2010 issued for European Application No. 08 77 7340 (corresponding to present U.S. application).
Hamada, Y., et al., "Novel non-peptidic and small-sized BACE1 inhibitors", Bioorganic & Medicinal Chemistry Letters, vol. 18, No. 5, Mar. 1, 2008, pp. 1654-1658.
International Search Report issued Aug. 26, 2008 in International (PCT) Application No. PCT/JP2008/061141.
International Preliminary Report on Patentability including English translation of PCT written opinion issued Jan. 21, 2010 in International (PCT) Application No. PCT/JP2008/061141.
Kimura, T. et al., "Design and Synthesis of Potent β-Secretase (BACE1) Inhibitors with P₁ Carboxylic Acid Bioisosteres", Bioorganic and Medicinal Chemistry Letters, 2006, vol. 16, pp. 2380-2386.
Sinha, S. et al., "Purification and Cloning of Amyloid Precursor Protein β-Secretase from Human Brain", Nature, 1999, vol. 402, pp. 537-540.
Tung, J.S. et al., "Design of Substrate-Based Inhibitors of Human β-Secretase", J. Med. Chem., 2002, vol. 45, pp. 259-262.

(Continued)

*Primary Examiner* — Rebecca Anderson
*Assistant Examiner* — Alicia L Otton
(74) *Attorney, Agent, or Firm* — Wenderoth, Lind & Ponack, L.L.P.

(57) ABSTRACT

A novel compound represented by the formula (1) below which has β-secretase inhibitory activity, its pharmaceutically acceptable salt or a prodrug thereof.

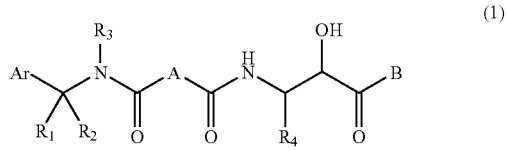

wherein Ar is a substituted or unsubstituted 5 to 6 membered mono cyclic aromatic group; $R_1$, $R_2$ and $R_3$ are hydrogen atom, substituted or unsubstituted alkyl group or the like, or $R_2$ and $R_3$ may be taken together with the adjacent nitrogen atom and carbon atom respectively to form a 3 to 6 membered ring; $R_4$ is $C_{1-6}$ alkyl group, $C_{1-6}$ alkyl group substituted by phenyl, phenylthio, or a hetero ring, or the like;
A is represented by the formula below:

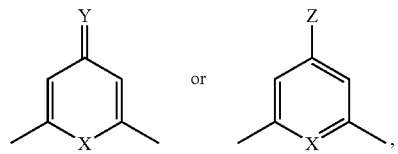

wherein X and Y are oxygen atom, NH or sulfur atom, Z is hydrogen atom, hydroxy group which may be substituted, amino group, thiol group, or the like; and B is hydroxy group, substituted or unsubstituted amino group, substituted or unsubstituted aliphatic or aromatic amino group, or the like.

4 Claims, No Drawings

OTHER PUBLICATIONS

Hom, R. et al., "Design and Synthesis of Hydroxyethylene-Based Peptidomimetic Inhibitors of Human β-Secretase", J. Med. Chem., 2004, vol. 47, pp. 158-164.

Stachel, S. et al., "Structure-Based Design of Potent and Selective Cell-Permeable Inhibitors of Human β-Secretase (BACE-1)", J. Med. Chem., 2004, vol. 47, pp. 6447-6450.

* cited by examiner

COMPOUND HAVING β-SECRETASE INHIBITORY ACTIVITY

TECHNICAL FIELD

The present invention relates to a novel compound having β-secretase inhibitory activity.

BACKGROUND ART

At present, in the development of drugs for preventing or treating Alzheimer's disease (abbreviated as AD) for which a fundamental therapeutic method has not been established, strategies targeted on secretases are main stream. Among them β-secretase and γ-secretase by which direct effect will be expected are especially paid attention. Therefore pharmaceutical companies and venture enterprises have recently extensively engaged in development of said inhibitors.

In 1999, it has been reported that β-secretase is a β-site APP cleaving enzyme BACE1 (also referred to as BACE, Asp2, or memapsin2), an aspartic acid protease, and β-secretase inhibitor based on the substrate transition state concept established by the study on the same class of protease inhibitors such as renin and HIV which belong to a family of an aspartic acid protease as 3-secretase does, have been reported. Any inhibitor is a peptide-based inhibitor by forming a substrate transition state analogue at a β-secretase cleaving site of mimics Swedish APP Swedish variant-type APP readily produces Aβ. Tung et al. for the first time determined the IC$_{50}$ value of 30 nM in a 14 residue peptide (P10-P4' statV) in which a hydroxyethylcarbonylisostere (statine) structure was introduced into a substrate cleaving site of β-secretase. They reported that other substrate transition state analogues (AH-PPA, ACHPA) could also inhibit β-secretase (for example, see patent literatures 1 and 2.). Ghosh et al. searched various compounds containing hydroxyethyleneisostere, and discovered that OM 99-2 and OM 003 had strong inhibitory activity (Ki=1.6 nM/Ki=0.3 nM respectively) (for example, see patent literature 1.).

The present inventors also designed BACE1 inhibitor KMI-008 as the translation state analogue using hydroxymethycarbonyl (HMC) isoster used in development of renin, HIV-protease inhibitor, or plasmepsin inhibitor which is a special enzyme of malaria protozoa, and using these compounds as a lead compound, KMI-358 and KMI-370 have been developed. Furthermore, BACE1 inhibitors KMI-429 and KMI-684 which are more excellent for chemical stability and more excellent in the inhibition activity have been found (See patent document 2.).

These compounds have strong BACE1 inhibiting activity, but have a peptide structure in their molecules, and therefore, it is supposed that they may be unstable to enzymes in a living body. Furthermore, in considering the action site of β-secretase inhibitor, the drug is necessary to pass through the blood brain barrier and therefore, there are many points to be considered in its development such as a molecular size and hydrophilic and hydrophobic valance.

To conquer these points, a lower molecular BACE1 wherein a part of peptide chin is substituted by an aromatic compound or isophthalic acid by foreign and domestic several research groups was reported (See Non patent 3 and Nonpatent 4.).

[Patent literature 1] WO 2001/000665
[Patent literature 2] WO 2004/076478
[Non patent literature 1] Nature, 402, 537-540 (1999)
[Non patent literature 2] J. Med. Chem., 45, 259-262 (2002)
[Non patent literature 3] J. Med. Chem., 47, 158 (2004)
[Non patent literature 4] J. Med. Chem., 47, 6447 (2004)

DISCLOSURE OF THE INVENTION

Problem to be Solved by Invention

The development of a compound that is stable for metabolic enzymes or hydrolytic enzymes in blood, has strong β-secretase inhibitory activity and is orally administrable for long terms as a therapeutic agent for Arzhemer's disease has been solicited.

Means for Solving the Problem

In the present invention, in order to develop a drug which has a smaller molecule, is stable in a living body and is orally administrable, three amino acid residues at N-terminus of KMI-429 and KMI-684 are substituted by an aromatic compound which is a non-peptide. In this case the conformation of the inhibitor which is bound to an active center of β-secretase based on the steric structure by X ray crystal analysis is speculated or expected by computational chemistry and then, by introducing to the inhibitor such an aromatic compound as stabilizes the conformation, β-secretase inhibitory activity was found to be unexpectedly increased and thus the present invention has been completed.

Namely the present invention is represented by the following formula (1):

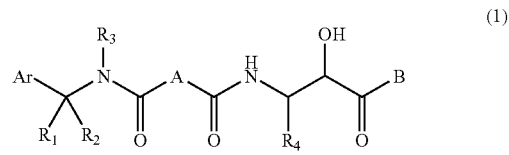

wherein Ar is a substituted or unsubstituted 5 to 6 membered mono cyclic aromatic group, and said aromatic group may have a hetero atom selected from nitrogen atom, oxygen atom and sulfur atom; $R_1$, $R_2$ and $R_3$ are hydrogen atom, substituted or unsubstituted alkyl group, substituted or unsubstituted allyl group, or substituted or unsubstituted aryl group, nitro group, halogen atom, cyano group, hydroxy group or its derivative, or carboxy group or its derivative, and $R_2$ and $R_3$ may be taken together with the adjacent nitrogen atom and carbon atom respectively to form a 3 to 6 membered ring which may be interrupted by oxygen atom, sulfur atom or substituted or unsubstituted amino group; and $R_4$ is $C_{1-6}$ alkyl group, $C_{2-6}$ alkenyl group, $C_{2-6}$ alkinyl group, $C_{3-7}$ cycloalkyl group, phenyl group, $C_{1-6}$ alkyl group substituted by phenyl, phenylthio or a hetero ring provided that said phenyl, said phenylthio and said hetero ring may be substituted by $C_{1-6}$ alkyl, hydroxy, nitro, halogen, —SO$_3$H or —PO$_4$H;

A is represented by the formula:

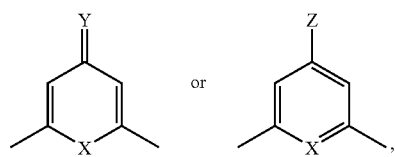

wherein X and Y are oxygen atom, NH or sulfur atom, Z is hydrogen atom, hydroxy group, amino group, or thiol group, and when Z is hydroxy group, amino group or thiol group, said group may be substituted by substituted or unsubstituted alkyl group, substituted or unsubstituted allyl group, or substituted or unsubstituted aryl group, substituted or unsubstituted acyl group, substituted or unsubstituted alkylsulfonyl group, substituted or unsubstituted arylsulfonyl group, or substituted or unsubstituted allylsulfonyl group; and B is hydroxy group, substituted or unsubstituted amino group, substituted or unsubstituted hydrazino group, substituted or unsubstituted hydroxyamino group, or substituted or unsubstituted aliphatic or aromatic amino group, or its pharmaceutically acceptable salt or a prodrug thereof.

The present invention also relates to a compound represented by the generic formula (1) wherein Ar is substituted or unsubstituted phenyl group, $R_1$, $R_2$ and $R_3$ are hydrogen atom, or substituted or unsubstituted alkyl group, or $R_2$ and $R_3$ may be taken together with the adjacent nitrogen atom and carbon atom respectively to form a 3 to 6 membered ring which may be interrupted by oxygen atom, sulfur atom, or substituted or unsubstituted amino group, or its pharmaceutically acceptable salt or a prodrug thereof.

The compound in case that in the generic formula (1), the following partial formula:

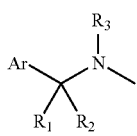

means the following formula:

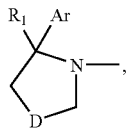

wherein D is methylene group, oxygen atom, sulfur atom, or substituted or unsubstituted imino group, and Ar and $R_1$ are the same as defined above, is especially preferable.

The present invention relates to the compound represented by the generic formula (1) wherein B is hydroxy group, substituted or unsubstituted amino group, or the following formula:

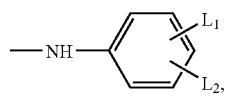

wherein $L_1$ and $L_2$ are hydrogen atom, substituted or unsubstituted alkyl group, substituted or unsubstituted allyl group, substituted or unsubstituted aryl group, nitro group, halogen atom, cyano group, hydroxy group or its derivative, carboxy group or its derivative, or group biologically equivalent to carboxyl group, or its pharmaceutically acceptable salt or a prodrug thereof.

The present invention relates to the compound represented by the generic formula (1) wherein in $B_1$ of B, either $L_1$ or $L_2$ is a group biologically equivalent to a carboxyl group which is selected from the following groups:

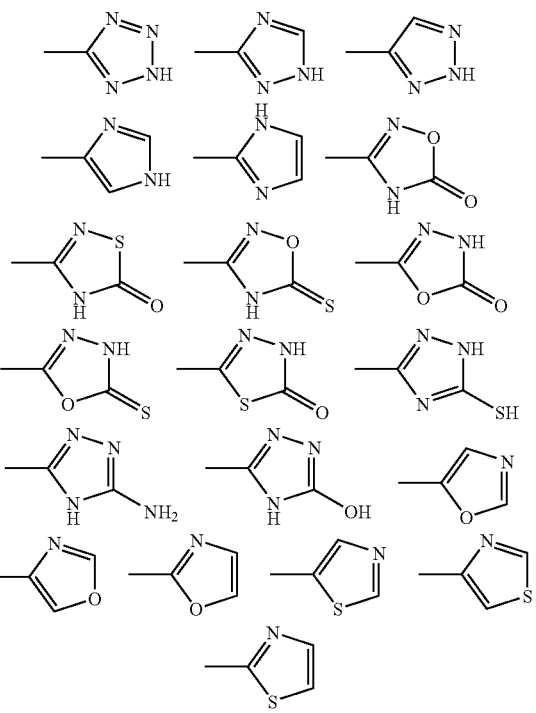

or its pharmaceutically acceptable salt or a prodrug thereof.

The present invention relates to the compound represented by the generic formula (1) wherein $R_4$ is a group selected from following groups:

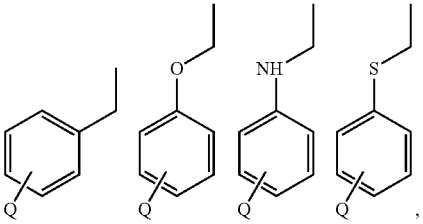

wherein Q is hydrogen atom, $C_{1-6}$ alkyl group, hydroxy group, nitro group, halogen atom, —$SO_3H$ or —$PO_4H$, or a pharmaceutically acceptable salt thereof.

The present invention also relates to a medicament or a β-secretase inhibitor containing the above compound as an active ingredient.

The present invention relates to an agent for preventing or treating (i) neurodegenerative disease, (ii) neuropathy in cerebrovascular disease, head trauma•spinal damage, encephalitis sequela, or cerebral palsy, (iii) memory disorder, or (iv) mental disease, associated with β-secretase containing the above compound as an active ingredient.

The present invention relates to an agent for preventing or treating (i) neurogenerative disease, (ii) neuropathy in cerebrovascular disease, head trauma•spinal damage, encephalitis sequela, or cerebral palsy, (iii) memory disorder or (iv) mental disease, by inhibiting production•secretion of a βamyloid protein, or inhibiting production•secretion of a βamyloid protein, containing the aforementioned compound as an active ingredient.

The present invention relates to an agent for treating the neurodegenerated disease, such as Alzheimer's disease or Parkinson's disease, containing the aforementioned compound as an active ingredient.

The present invention relates to an agent for inhibiting production•secretion of a βamyloid protein.

The present invention relates to an agent for preventing or treating neuropathy or mental disease in head trauma•spinal damage, encephalitis sequela, or cerebral palsy containing the aforementioned compound as an active ingredient.

The present invention also relates to a method for treating (i) neurogenerative disease, (ii) neuropathy in cerebrovascular disease, head trauma•spinal damage, encephalitis sequela, or cerebral palsy, (iii) memory disorder, or (iv) mental disease associated with β-secretase, which comprises administering an effective amount of a β-secretase inhibitor containing the aforementioned compound as an active ingredient to a mammal.

The "prodrug" used in the present specification refers to a compound which is chemically or biologically hydrolyzed, reduced or oxidized in a living body, and reproduces the compound of the present invention. The prodrug of the present invention includes compounds which are prepared by any procedure for converting into a prodrug known to a person skilled in the art. For example, when the compound of the present invention has a carboxyl group or an amino group, compounds in which those groups are derived into an ester group or an amide group easily hydrolysable in a living body correspond to a prodrug. When a compound has a carboxyl group, examples of the prodrug include compounds in which the carboxyl group is introduced into alkyl such as methyl, and ethyl, alkyloxyalkyl such as methyloxymethyl, ethyloxymethyl, 2-methyloxyethyl, and 2-methyloxyethyloxymethyl, acyloxymethyl such as pivaloyloxymethyl, acetyloxymethyl, cyclohexylacetyloxymethyl, and 1-methylcyclohexylcarbonyloxymethyl, alkoxycarbonylalkyl such as ethyloxycarbonyloxy-1-ethyl, or cycloalkyloxycarbonylalkyl such as cyclohexyloxycarbonyloxy-1-ethyl. When a compound has an amino group, examples of a prodrug include compounds in which an amino group is introduced into acetamide.

The compound (1) of the present invention can be formed in a pharmaceutically acceptable salt thereof. Examples of the salt include an acid addition salt and a base addition salt. Examples of the acid addition salt include inorganic acid salts such as hydrochloride, hydrobromide, sulfate, etc. and organic acid salts such as citrate, oxalate, malate, tartarate, fumarate, maleate, etc. and examples of a base addition salt include inorganic base salts such as a sodium salt, a calcium salt, etc. and organic base salts such as a meglumine salt, a trishydroxymethylaminomethane salt, etc. In addition, the compound of the present invention includes a hydrate and a solvate of the compound (1) or a pharmaceutically acceptable salt thereof.

The compound of the present invention can be prepared by the following method or a similar method.

An amide linkage (s) contained in the compound of the present invention can be prepared by the method which is conventionally used in peptide chemistry, for example, the method described in "The Peptides", vol. 1, by Schroder and Luhker, Academic Press, New York, U.S.A (1966), and "Base and Experiment of Peptide Synthesis" by Nobuo Izumiya, et al., Maruzen (1985).

The condensation method to form an amide linkage can be exemplified by the azide, acid chloride, acid anhydride, carbodiimide, carbodiimide-active, active ester, carbonylimidazole, redox, or enzyme method, and a method using Woodward's reagent K.

The compound (1) of the present invention can be prepared, for example by using the above condensing agent according to the following method.

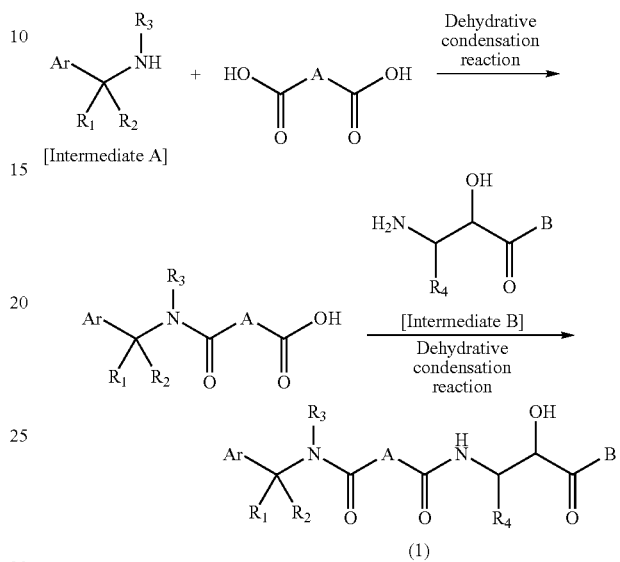

[Intermediate A]

[Intermediate B]

(1)

wherein each signal is the same as defined above.

Amine derivatives shown by above intermediate A can be synthesized by known synthetic methods described for example in JIKKEN KAGAKU KOUZA, Vol. 14, Synthesis of Organic compounds II, edited by The Chemical Society of Japan, by Maruzen. Example for preparing intermediate A in case that $R_2$ and $R_3$ form a ring is shown below.

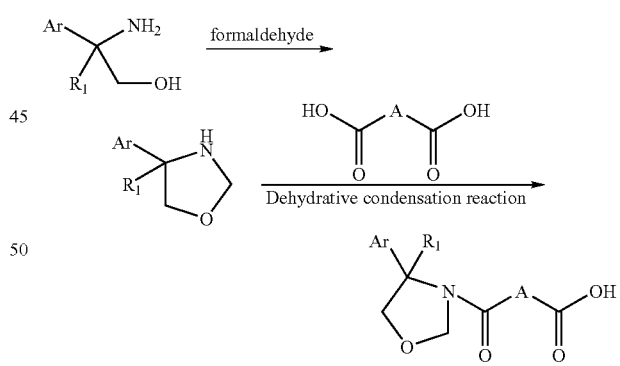

wherein above each signal is the same as defined above.

Above intermediate B is for example, prepared by the following synthesizing method.

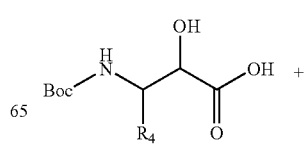

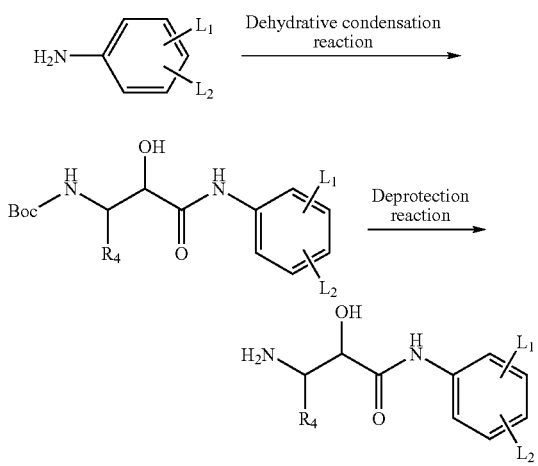

wherein each signal is the same as define above.

Before carrying out these condensation reactions, carboxyl group or amino group, hydroxy group or amidino group, etc. which does not participate in said condensation reaction may be protected by a conventional method.

To protect a functional group not involved in the condensation reactions, the functional group can be protected with a protecting group which is usually used in organic chemistry, or a protecting group described, for example, in "Protective Groups in Organic Synthesis", by Green, John Wiley & Sons, Inc. (1981).

The condensation reaction is usually performed in a solvent. Examples of solvents include chloroform, dichloromethane, ethyl acetate, N,N-dimethylformamide, dimethyl sulfoxide, pyridine, dioxane, tetrahydrofuran, N-methylpyrrolidone, water, methanol, and a mixture thereof. The condensation reaction is carried out at a range of −30 to 50° C. as in conventional cases.

Furthermore, the protecting group, after reaction can be eliminated with various methods according to the kind of the protecting group without giving any influence on other functional group than the protecting group. Examples include acid treatment with hydrogen chloride, hydrogen bromide, anhydrous hydrogen fluoride, methanesulfonic acid, trifluoromethanesulfonic acid, trifluoroacetic acid, or a mixture thereof, alkali treatment with sodium hydroxide, potassium hydroxide, hydrazine, diethylamine, or piperidine, sodium treatment in liquid ammonia, reduction with palladium carbon, and treatment with a silylating agent such as trimethylsilyl triflate, trimethylsilyl bromide, etc. In a deprotecting reaction by the treatment with the acid or the silylating agent mentioned above, it is preferable to add a cation scavenger such as anisole, phenol, cresol, anisole, thioanisole, ethanedithiol, etc. to efficiently perform the deprotecting reaction.

Thus prepared compound of the present invention can be subjected to conventional separation and purification after completion of the aforementioned series of reactions. For example, by extraction, distribution, re-precipitation, recrystallization, column chromatography, etc., the compound of the present invention can be obtained in a purer form.

The compound of the present invention has asymmetry in some cases, or has a substituent having an asymmetric carbon in some cases, such that there is an optical isomer. The compound of the present invention includes a mixture of the respective or isolated isomers. Examples of a method for obtaining such optical isomer pure include optical resolution.

As the optical resolution, the compound of the present invention or an intermediate thereof may form a salt with an optically active acid (e.g. monocarboxylic acids such as mandelic acid, N-benzyloxyalanine, lactic acid, etc., dicarboxylic acids such as tartaric acid, o-diisopropylidenetartaric acid, malic acid, etc., sulfonic acids such as camphorsulfonic acid, bromocamphorsulfonic acid, etc.) in an inert solvent (e.g. alcohol solvents such as methanol, ethanol, and 2-propanol, ether solvents such as diethyl ether, ester solvents such as ethyl acetate, aromatic hydrocarbon solvents such as toluene, acetonitrile, and a mixed solvent thereof).

In addition, when the compound of the present invention or an intermediate thereof has an acidic substituent such as a carboxyl group, it may be formed as a salt with optically active amines (e.g. organic amines such as α-phenethylamine, quinine, quinidine, cinchonidine, cinchonine, strychnine, etc.).

The compound of the present invention can be orally or parenterally administered. In case of oral administration, the usual dosage form can be used. In case of parenteral administration, the preparation is used in the form of local administration, injection, dermal administration, nasal administration and so on.

The above dosage form is formulated into a preparation with a pharmaceutically acceptable excipient or additive by conventional methods. Examples of a pharmaceutically acceptable excipient or additive include a carrier, binder, flavor, buffer, thickener, colorant, stabilizer, emulsifier, dispersant, suspending agent, and antiseptic.

Examples of a pharmaceutically acceptable carrier include magnesium carbonate, magnesium stearate, talc, sugar, lactose, pectin, dextrin, starch, gelatin, tragacanth, methylcellulose, sodium carboxymethylcellulose, low melting point wax, cacao butter and so on. A capsule can be formulated by putting the compound of the present invention together with a pharmaceutically acceptable carrier therein. The compound of the present invention can be added into a capsule by mixing with a pharmaceutically acceptable excipient, or without the excipient. A cachet can be prepared by similar methods.

Examples of a liquid preparation for injection include a solution, suspension, emulsion, etc. such as an aqueous solution, or water-propylene glycol solution. The liquid preparation may be also prepared in the form of a solution of polyethylene glycol or/and propylene glycol, which may contain water. A liquid preparation suitable for oral administration can be prepared by adding water and, if necessary, a colorant, flavor, stabilizer, sweetener, solubilizer and thickener to the compound of the present invention. A liquid preparation suitable for oral preparation may be prepared by adding the compound of the present invention or a pharmaceutically acceptable salt thereof together with a dispersant to water to increase its viscosity. Examples of a thickener include pharmaceutically acceptable natural or synthetic gum, resin, methylcellulose, sodium carboxymethylcellulose or known suspending agent, etc.

Examples of an agent for topical application include the aforementioned liquid preparation, and a cream, aerosol, spray, powder, lotion, and ointment. The above agent for topical application can be prepared by mixing the compound of the present invention or a pharmaceutically acceptable salt thereof with a pharmaceutically acceptable diluent and carrier that are conventionally used. An ointment or cream is prepared, for example, by adding a thickener and/or a gelling agent to an aqueous or oily base. Examples of a base include water, liquid paraffin, and vegetable oil (peanut oil, castor oil). Examples of a thickener include soft paraffin, aluminum stearate, cetostearyl alcohol, propylene glycol, polyethylene glycol, lanolin, hydrogenated lanolin, beeswax, etc.

A lotion can be prepared by adding one or more kinds of pharmaceutically acceptable stabilizer, suspending agent, emulsifier, diffusing agent, thickener, colorant, and flavor to an aqueous or oily base.

A powder is formulated into a preparation with a base for a pharmaceutically acceptable powder. Examples of a powder include talc, lactose, starch, etc. A drop can be formulated into a preparation with an aqueous or non-aqueous base and one or more kinds of pharmaceutically acceptable diffusing agent, suspending agent, and solubilizer.

The agent for topical application may contain an antiseptic such as methyl hydroxybenzoate, propyl hydroxybenzoate, chlorocresol and benzalkonium chloride, or a bacteriostat.

A preparation of a liquid spray, a powder or a drop containing the compound of the present invention or a pharmaceutically salt thereof as an active ingredient can be administered nasally.

The dose and administration interval are variant depending on symptoms, age, body-weight, and administration form and, when orally administered, usually a range of about 1 to about 500 mg, preferably a range of about 5 to about 100 mg per adult per day, which can be administered once or in divided doses. When administered as an injection, a range of about 0.1 to about 300 mg, preferably a range of about 1 to about 100 mg can be administered once or in divided doses.

A process for preparing the compound of the present invention will be explained below by Examples and Reference examples, but should not be limited by them.

When the present reaction is performed, the technique of protection and deprotection can be used, if necessary. The technique of protection and deprotection is described in detail in the aforementioned Protective Groups in Organic Synthesis [authored by Green, John Wiley 86 Sons, Inc. (1981)].

EXAMPLE

The meanings of abbreviations used in Examples or Reference examples are as follows:

Boc: tert-butoxycarbonyl group

EDC.HCl: 1-ethyl-3-(3-dimethylaminopropyl)carbodiimide

BOP: bezotriazol-1-yl-oxy-tris(dimethylamino)-phosphonium hexafluorophosphate

Fmoc: 9-fluorenylmethoxycarbonyl group

HOBT: N-hydroxybenzotriazole

DMF: N,N'-dimethylformamide

THF: tetrahydrofuran

Apns: amino acid residue of (2S,3S)-3-amino-2-hydroxy-4-phenylbutanoic acid

Boc-Apns-OH which was used in the following Examples or Reference examples can be prepared, for example according to the synthesizing method described in Journal of Medicinal Chemistry Vol. 20, p 510-515, (1977).

Reference Example 1

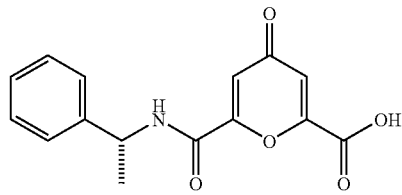 [SMILES: C[C@@H](NC(=O)c1cc(=O)cc(C(=O)O)o1)c1ccccc1]

(R)-1-Phenethyamine (200 mg, 1.65 mmol) and chelidonic acid (456 mg, 2.48 mmol) were dissolved in DMF, and thereto were added HOBT (380 mg, 2.48 mmol) and EDC.HCl (480 mg, 2.48 mmol), followed by stirring for 12 hours. After reaction, the reaction mixture was concentrated under reduced pressure, acidified with 1N hydrochloric acid, and extracted with ethyl acetate. The organic layer was dried over anhydrous magnesium sulfate, concentrated in vacuo, and purified with reversed phase chromatography under moderate pressure to give the object compound (a compound shown in the above formula: it is abbreviated as the object compound hereafter) as a white powder.

Yield, 83%; EI-MS m/z: 286.06 (M−H)⁻.

Reference Example 2

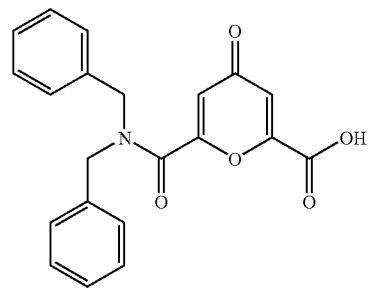 [SMILES: O=C(O)c1cc(=O)cc(C(=O)N(Cc2ccccc2)Cc2ccccc2)o1]

Chelidonic acid monohydrate (100 mg, 0.50 mmol) and N-methylmorpholine (109 μL, 0.99 mmol) were dissolved in dried THF (5 mL), and thereto under stirring at −15° C., was added isobutyl chloroformate (79.3 μL, 0.50 mmol). After 15 minutes benzylamine (95.2 μL, 0.50 mmol) was added thereto. After reacting at room temperature for 15 hours, ethyl acetate was added thereto. The organic layer was washed with aqueous citric solution, extracted with an aqueous sodium hydrogen carbonate solution and extracted with ethyl acetate after acidifying with citric acid. After washing with saturated brine, the solution was dried over anhydrous magnesium sulfate, and concentrated in vacuo to give the object compound as a white powder.

Yield, 30%; EI-MS m/z: 362.18 (M−H)⁻.

Reference Example 3

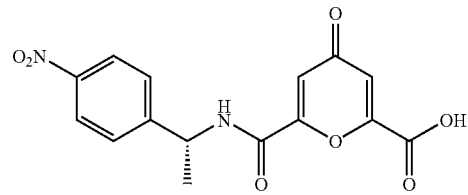 [SMILES: C[C@@H](NC(=O)c1cc(=O)cc(C(=O)O)o1)c1ccc([N+](=O)[O-])cc1]

(R)-1-(4-Nitrophenyl)ethylamine (100 mg 0.49 mmol) and chelidonic acid monohydrate (100 mg, 0.49 mmol) were dissolved in DMF, and to the solution were added triethyamine (137 µL, 0.99 mmol) and BOP (219 mg, 0.49 mmol), followed by stirring for 12 hours. After reaction, the reaction mixture was concentrated in vacuo, and to the residue was added ethyl acetate. The organic layer was washed with an aqueous 10% citric acid solution and saturated brine, dried over anhydrous magnesium sulfate. After concentration in vacuo, there was obtained the object compound as a yellow oil.

Yield, 100% (a crude product); EI-MS m/z: 331.16 (M–H)⁻.

Reference Example 4

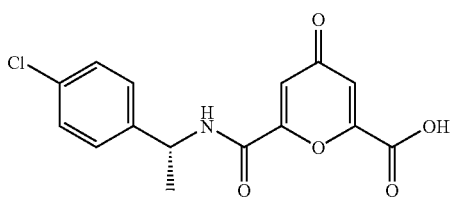 [SMILES: C[C@@H](NC(=O)c1cc(=O)cc(C(=O)O)o1)c1ccc(Cl)cc1]

The object compound as yellow oil was synthesized using (R)-1-(4-chlorophenyl)ethylamine and chelidonic acid monohydrate according to the procedure described in Reference example 3.

Yield, 100% (as a crude product); EI-MS m/z: 319.96 (M–H)⁻.

Reference Example 5

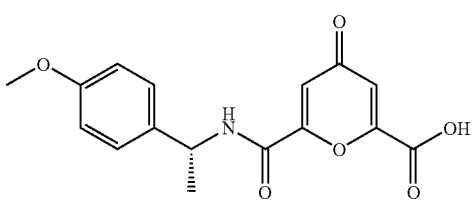 [SMILES: COc1ccc([C@@H](C)NC(=O)c2cc(=O)cc(C(=O)O)o2)cc1]

The object compound was synthesized as a yellow oil using (R)-1-(3-methoxyphenyl)ethylamine and chelidonic acid monohydrate according to the procedure described in Reference example 3.

Yield, 56%; EI-MS m/z: 316.16 (M–H)⁻.

Reference Example 6

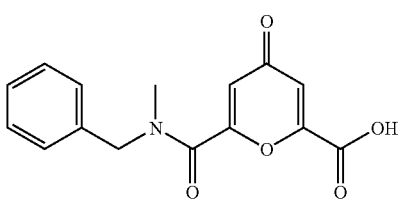 [SMILES: CN(Cc1ccccc1)C(=O)c1cc(=O)cc(C(=O)O)o1]

The object compound was synthesized as a yellow oil using N-methylbenzylamine and chelidonic acid monohydrate according to the procedure described in Reference example 3.

Yield, 100% (as a crude product); EI-MS m/z: 285.95 (M–H)⁻.

Reference Example 7

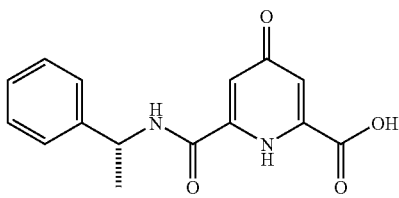 [SMILES: C[C@@H](NC(=O)c1cc(=O)cc(C(=O)O)[nH]1)c1ccccc1]

The object compound was synthesized as a yellow oil using (R)-1-phenethyamine and chelidamic acid monohydrate according to the procedure described in Reference example 1. The crude product was purified by reversed phase chromatography under moderate pressure to give the object compound as a white powder.

Yield, 75%; EI-MS m/z: 285.05 (M–H)⁻.

Reference Example 8

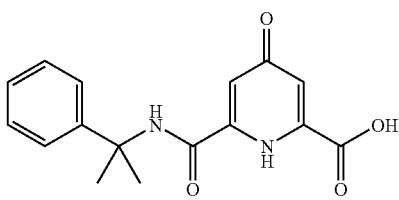 [SMILES: CC(C)(NC(=O)c1cc(=O)cc(C(=O)O)[nH]1)c1ccccc1]

The object compound was synthesized as a yellow oil using α-dimethylbenzylamine and chelidamic acid monohydrate according to the procedure described in Reference example 1. The crude product was purified by reversed phase chromatography under moderate pressure to give the object compound as a white powder.

Yield, 81%; EI-MS m/z: 299.21 (M–H)⁻.

Reference Example 9

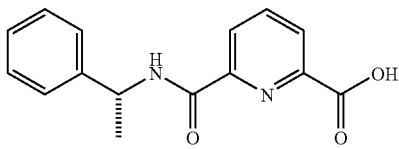 [SMILES: C[C@@H](NC(=O)c1cccc(C(=O)O)n1)c1ccccc1]

The object compound was synthesized as a yellow oil using (R)-1-phenethyamine and 2,6-pyridine dicarboxylic acid according to the procedure described in Reference example 1. The crude product was purified by reversed phase chromatography under moderate pressure to give the object compound as a white powder.

Yield, 73%; EI-MS m/z: 269.01 (M–H)⁻.

Reference Example 10

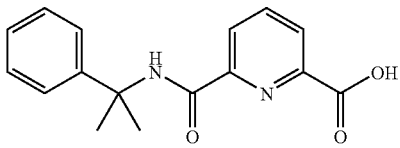 [SMILES: CC(C)(NC(=O)c1cccc(C(=O)O)n1)c1ccccc1]

The object compound was synthesized as a yellow oil using α-dimethylbenzylamine and 2,6-pyridine dicarboxylic acid according to the procedure described in Reference example 1. The crude product was purified by reversed phase chromatography under moderate pressure to give the object compound as a white powder.

Yield, 77%; EI-MS m/z: 283.11 (M−H)⁻.

Reference Example 11

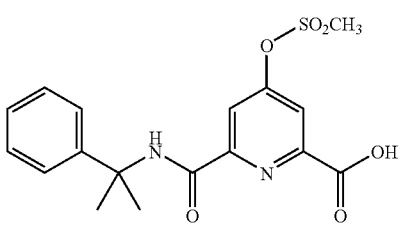 [SMILES: CC(C)(NC(=O)c1cc(OS(C)(=O)=O)cc(C(=O)O)n1)c1ccccc1]

Compound (20 mg, 0.07 mmol) of Reference example 8 and methanesulfonyl chloride (15 mg, 0.133 mmol) were dissolved in THF 2 ml. Thereto was added triethyamine (55 μl, 0.40 mmol), followed by stirring for 12 hours. The reaction solution was acidified with 1N hydrochloric acid and extracted with ethyl acetate. The extract was dried over magnesium sulfate and concentrated in vacuo to give the crude product of the object compound as an oil. The product was served as a synthetic intermediate without purification.

Yield, 100% (as a crude product); EI-MS m/z: 377.26 (M−H)⁻.

Reference Example 12

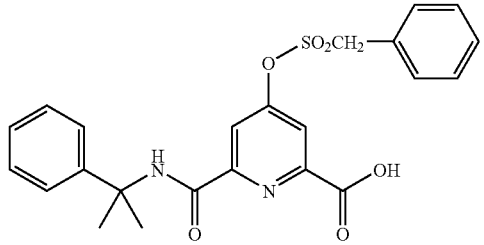

The object compound in a crude product was synthesized as an oil using compound of Reference example 8 and benzylsulfonyl chloride according to above procedure. The crude product was used as a synthetic intermediate.

Yield, 100% (as a crude product); EI-MS m/z: 453.00 (M−H)⁻.

Reference Example 13

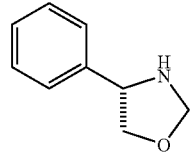 [SMILES: c1ccc([C@H]2COCN2)cc1]

(S)-Phenylglycinol (2 g, 14.6 mmol) was dissolved in purified water 100 ml. To the solution was dropped 38% formaldehyde solution (1.2 ml, 14.6 mmol) in an ice bath. After stirring at room temperature for 12 hours, the resulting crystals were filtered under suction to give the object compound as a white powder.

Yield, 85%; EI-MS m/z: 150.03 (M+H)⁺.

Reference Example 14

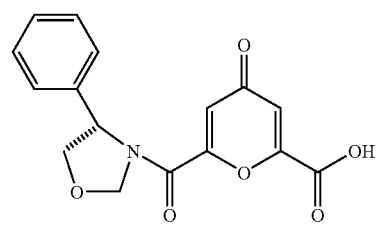 [SMILES: O=C(O)c1cc(=O)cc(C(=O)N2COC[C@@H]2c2ccccc2)o1]

Compound (200 mg, 1.34 mmol) of Reference example 13 and chelidonic acid (370 mg, 2 mmol) were dissolved in DMF. Thereto were added HOST (286 mg, 2 mmol) and EDC.HCl (383 mg, 2 mmol), followed by stirring for 12 hours at room temperature. After reaction, the reaction mixture was concentrated in vacuo, extracted with ethyl acetate, and washed with 1N hydrochloric acid and saturated brine. The organic layer was dried, concentrated in vacuo, and the residue was purified by reversed phase chromatography under moderate pressure to give the object compound as white powder.

Yield, 54%; EI-MS m/z: 316.13 (M+H)⁺.

Reference Example 15

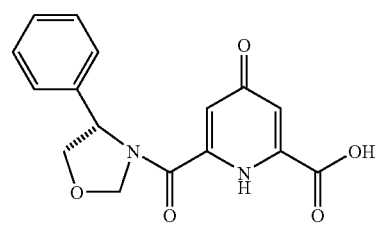 [SMILES: O=C(O)c1cc(=O)cc(C(=O)N2COC[C@@H]2c2ccccc2)[nH]1]

The object compound in a crude product was synthesized using compound (200 mg, 1.34 mmol) of Reference example 13 and chelidamic acid (368 mg, 2 mmol) according to above procedure. The crude product was purified by reversed phase chromatography under moderate pressure to give the object compound as a white powder.

Yield, 62%; EI-MS m/z: 315.24 (M+H)⁺.

Reference Example 16

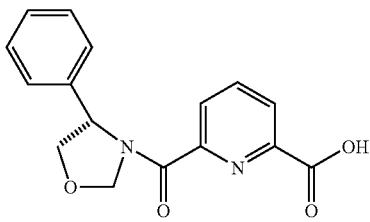 [SMILES: O=C(O)c1cccc(C(=O)N2COC[C@@H]2c2ccccc2)n1]

The object compound in a crude product was synthesized using compound (200 mg, 1.34 mmol) of Reference example 13 and 2,6-pyridine dicarboxylic acid (334 mg, 2 mmol) according to above procedure. The crude product was purified by reversed phase chromatography under moderate pressure to give the object compound as a white powder.

Yield, 57%; EI-MS m/z: 299.15 (M+H)$^+$.

Reference Example 17

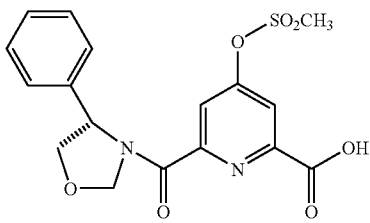 [SMILES: CS(=O)(=O)Oc1cc(C(=O)O)nc(C(=O)N2COC[C@@H]2c2ccccc2)c1]

Compound (20 mg, 0.06 mmol) of Reference example 16 was dissolved in THF, and thereto were added methanesulfonyl chloride (14 mg, 1.12 mmol) and triethyamine (33 µl, 0.24 mmol), followed by stirring at room temperature for 8 hours. To the reaction mixture was added methanol (50 ml), and the mixture was concentrated in vacuo. The residue was dissolved in ethyl acetate, and the solution was washed with 1N hydrochloric acid, dried over anhydrous magnesium sulfate. The organic layer was concentrated in vacuo to give a crude product as an oil. The product can be used as a synthetic intermediate without purification.

Yield, 100% (as a crude product); EI-MS m/z: 393.01 (M+H)$^+$.

Reference Example 18

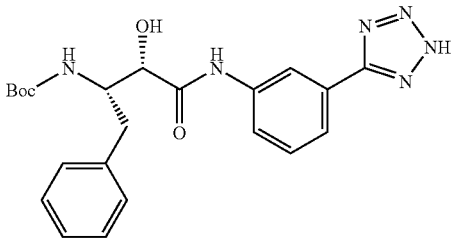 [SMILES: CC(C)(C)OC(=O)N[C@@H](Cc1ccccc1)[C@H](O)C(=O)Nc1cccc(-c2nn[nH]n2)c1]

Boc-Apns-OH (500 mg, 1.62 mmol) and 5-(3-amonophenyl)tetrazole (293 mg, 1.62 mmol) were dissolved in DMF, and thereto were added HOST (248 mg, 1.62 mmol) and EDC.HCl (373 mg, 1.94 mmol), followed by stirring at room temperature for 12 hours. After reaction the reaction mixture was concentrated in vacuo. To the residue were added ethyl acetate and 1N hydrochloric acid to crystallize. After drying in vacuo, resulting crystals were filtered by suction and washed with ethyl acetate, 1N hydrochloric acid and purified water, sequentially. The crystals were dried in vacuo to give the object compound as a white powder.

Yield, 76%; EI-MS m/z: 439.32 (M+H)$^+$.

Reference Example 19

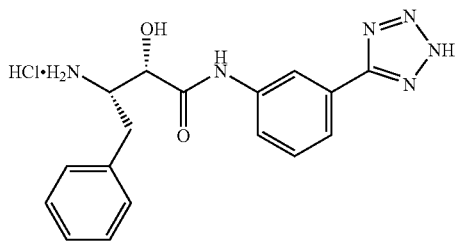

Compound (500 mg, 1.33 mmol) of Reference example 18 was dissolved in 4N hydrochloric acid/dioxane, followed by stirring at room temperature for 2 hours. After reaction, the solution was distilled in vacuo. To the residue was added hexane to crystallize. The crystals were washed with hexane, and dried in vacuo to give the objective compound as a white powder.

Yield, 99%; EI-MS m/z: 339.26 (M+H)$^+$.

Reference Example 20

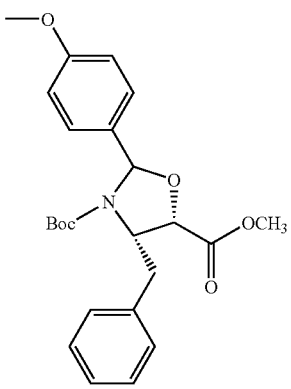

To a solution of Boc-Apns-OH (200 mg, 0.65 mmol) in methanol-pyridine (1:1) was added EDC.HCl (156 mg, 0.78 mmol), followed by stirring at room temperature for 12 hours. After concentration in vacuo, the residue was dissolved in ethyl acetate, washed with 5% sodium hydrogen carbonate solution, dried and concentrated in vacuo. The residue was dissolved in benzene and thereto were added p-anisaldehyde dimethylacetal (0.78 mmol) and pyridine p-toluenesulfonate (0.08 mmol), followed by refluxing for 3 hours. After reaction, the reaction mixture was extracted with ethyl acetate and washed with 1N hydrochloric acid, and saturated brine, sequentially. The organic layer was dried and then concentrated in vacuo. The residue was purified by silica gel chromatography to give the object compound as a white powder.

Yield, 73%; EI-MS m/z: 428.15 (M+H)$^+$.

Reference Example 21

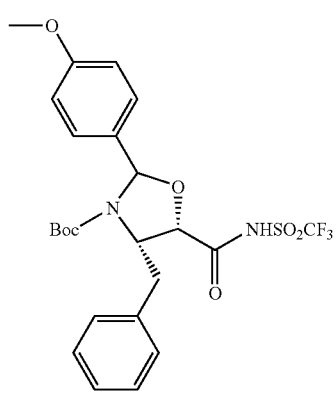

Compound (200 mg, 0.65 mmol) of Reference example 20 was dissolved in methanol, and thereto was added 1N sodium hydroxide, followed by stirring for 12 hours. The reaction mixture was concentrated in vacuo and acidified with 1N hydrochloric acid, and extracted with ethyl acetate. The organic layer was dried and then concentrated in vacuo. The residue was dissolved in DMF. Thereto were added trifluoromethanesulfonamide (145 mg, 0.98 mmol), catalytic amount of 4-dimethylaminopyridine (20 mg) and EDC.HCl (150 mg, 0.78 mmol), followed by stirring at room temperature for 12 hours. After reaction, the mixture was concentrated in vacuo, extracted with ethyl acetate and washed with 1N hydrochloric acid and saturated brine. The organic layer was dried and then concentrated in vacuo. The residue was purified by silica gel chromatography to give the object compound as a white powder.

Yield, 54%; EI-MS m/z: 545.07 (M+H)$^+$.

Reference Example 22

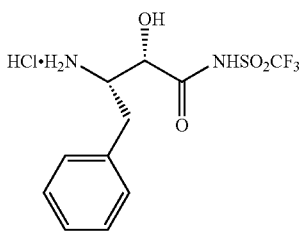

Compound (300 mg, 0.70 mmol) of Reference example 21 was dissolve in 4N hydrochloric acid/dioxane, followed by stirring at room temperature for 2 hours. After reaction, the mixture was concentrated in vacuo, and to the residue was added hexane to crystallize. The crystals were washed with hexane, and dried in vacuo to give the object compound as a white powder.

Yield, 99%; EI-MS m/z: 327.14 (M+H)$^+$.

Example 1

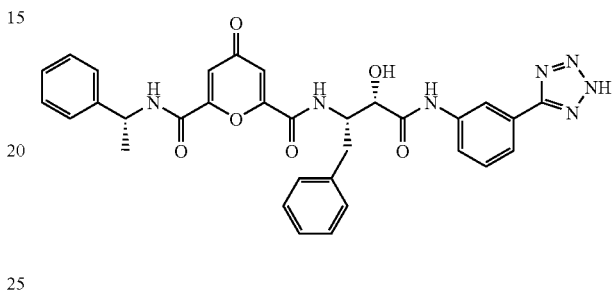

Compound of Reference example 1 (11 mg, 0.040 mmol) and compound of Reference example 19 (16 mg, 0.044 mmol) were dissolved in DMF, and thereto were added triethyamine (14 µL, 0.100 mmol) and BOP (26 mg, 0.06 mmol), followed by stirring for 12 hours. After reaction the reaction mixture was concentrated in vacuo, and thereto was added ethyl acetate. The organic layer was washed with an aqueous 10% citric acid solution and saturated brine, and dried over anhydrous magnesium sulfate. After concentrated in vacuo, to the residue was added hexane to crystallize. The crude product was purified by preparative HPLC to give the object compound as a white powder.

Yield, quantitative; purity, >98% by analytical HPLC (Rt, 26.18 min); TOF-MS m/z: 608.76 (M+H)$^+$.

Example 2

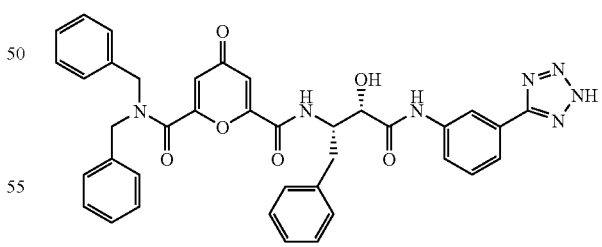

The object compound in a crude product was synthesized using compound of Reference example 2 and compound of Reference example 19 according to the procedure described in Example 1. The crude product was purified by preparative HPLC to give the object compound as a white powder.

Yield, quantitative; purity, >98% by analytical HPLC (Rt, 30.03 min); TOF-MS m/z: 684.688 (M+H)$^+$.

Example 3

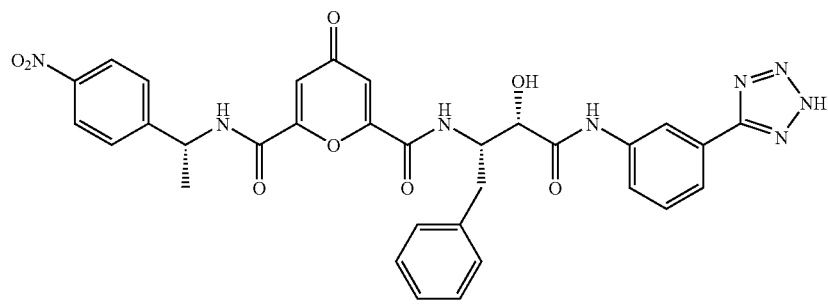 [SMILES: C[C@@H](NC(=O)c1cc(=O)cc(C(=O)N[C@@H](Cc2ccccc2)[C@H](O)C(=O)Nc2cccc(-c3nn[nH]n3)c2)o1)c1ccc([N+](=O)[O-])cc1]

The object compound in a crude product was synthesized using compound of Reference example 3 and compound of Reference example 19 according to the procedure described in Example 1. The crude product was purified by preparative HPLC to give the object compound as a white powder.

Yield, quantitative; purity, >98% by analytical HPLC (Rt, 26.28 min); TOF-MS m/z: 654.62 (M+H)$^+$.

Example 4

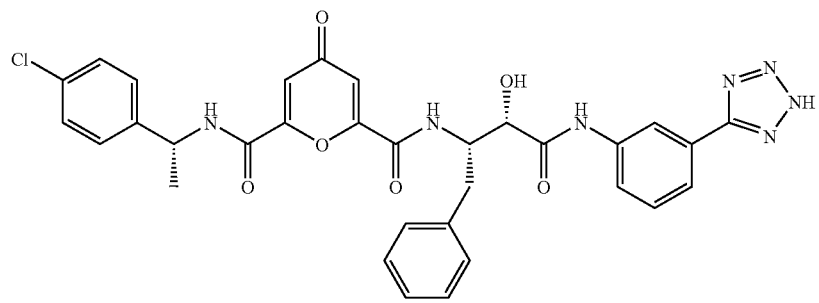 [SMILES: C[C@@H](NC(=O)c1cc(=O)cc(C(=O)N[C@@H](Cc2ccccc2)[C@H](O)C(=O)Nc2cccc(-c3nn[nH]n3)c2)o1)c1ccc(Cl)cc1]

The object compound in a crude product was synthesized using compound of Reference example 4 and compound of Reference example 19 according to the procedure described in Example 1. The crude product was purified by preparative HPLC to give the object compound as a white powder.

Yield, 93%; purity, >98% by analytical HPLC (Rt, 27.72 min); TOF-MS m/z: 642.19 (M+H)$^+$.

Example 5

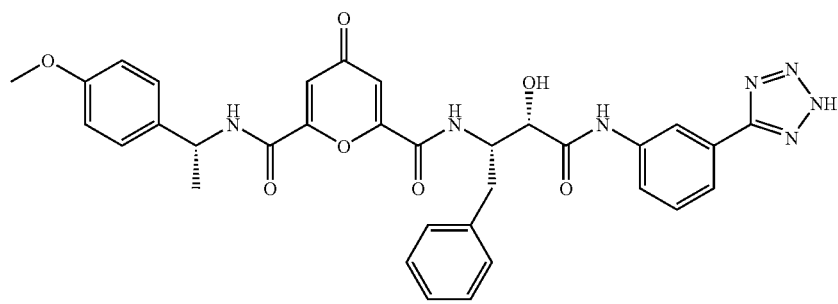 [SMILES: COc1ccc([C@@H](C)NC(=O)c2cc(=O)cc(C(=O)N[C@@H](Cc3ccccc3)[C@H](O)C(=O)Nc3cccc(-c4nn[nH]n4)c3)o2)cc1]

The object compound in a crude product was synthesized using compound of Reference example 5 and compound of Reference example 19 according to the procedure described in Example 1. The crude product was purified by preparative HPLC to give the object compound as a white powder.

Yield, quantitative; purity, >98% by analytical HPLC (Rt, 26.31 min); TOF-MS m/z: 638.81 (M+H)$^+$.

Example 6

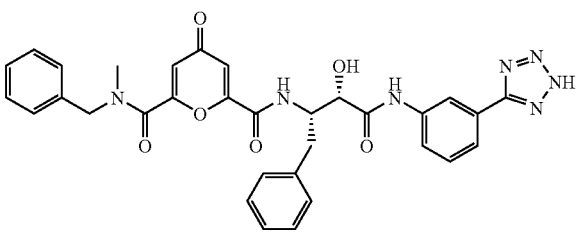

The object compound in a crude product was synthesized using compound of Reference example 6 and compound of Reference example 19 according to the procedure described in Example 1. The crude product was purified by preparative HPLC to give the object compound as a white powder.

Yield, 86%; purity, >98% by analytical HPLC (Rt, 26.08 min); TOF-MS m/z: 608.52 (M+H)$^+$.

Example 7

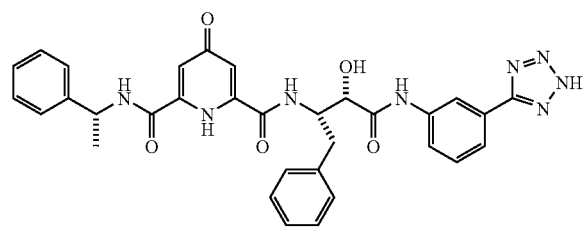

The object compound in a crude product was synthesized using compound of Reference example 7 and compound of Reference example 19 according to the procedure described in Example 1. The crude product was purified by preparative HPLC to give the object compound as a white powder.

Yield, 44%; purity, >98% by analytical HPLC (Rt, 23.97 min); TOF-MS m/z: 607.507 (M+H)$^+$.

Example 8

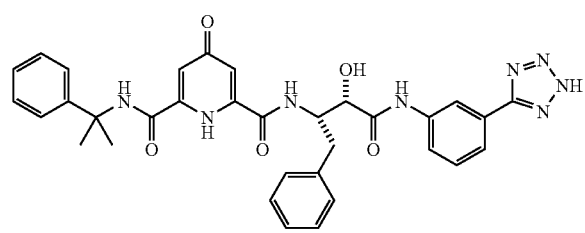

The object compound in a crude product was synthesized using compound of Reference example 8 and compound of Reference example 19 according to the procedure described in Example 1. The crude product was purified by preparative HPLC to give the object compound as a white powder.

Yield, 53%; purity, >98% by analytical HPLC (Rt, 24.75 min); TOF-MS m/z: 621.659 (M+H)$^+$.

Example 9

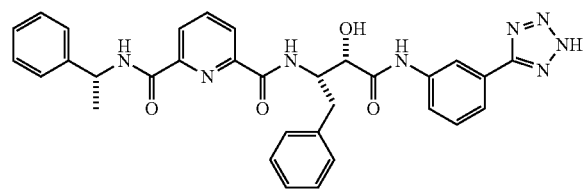

The object compound in a crude product was synthesized using compound of Reference example 9 and compound of Reference example 19 according to the procedure described in Example 1. The crude product was purified by preparative HPLC to give the object compound as a white powder.

Yield, 48%; purity, >98% by analytical HPLC (Rt, 24.61 min); TOF-MS m/z: 591.573 (M+H)$^+$.

Example 10

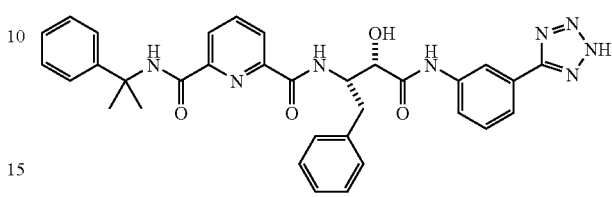

The object compound in a crude product was synthesized using compound of Reference example 10 and compound of Reference example 19 according to the procedure described in Example 1. The crude product was purified by preparative HPLC to give the object compound as a white powder.

Yield, 44%; purity, >98% by analytical HPLC (Rt, 25.13 min); TOF-MS m/z: 627.584 (M+Na)$^+$.

Example 11

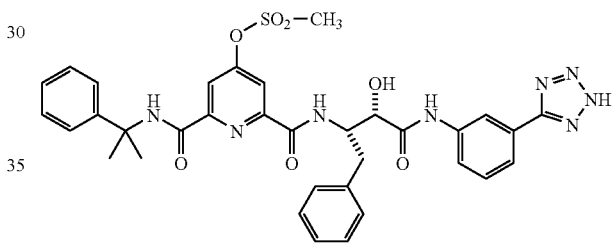

The object compound in a crude product was synthesized using compound of Reference example 11 and compound of Reference example 19 according to the procedure described in Example 1. The crude product was purified by preparative HPLC to give the object compound as a white powder.

Yield, 45%; purity, >98% by analytical HPLC (Rt, 25.48 min); TOF-MS m/z: 721.733 (M+Na)$^+$.

Example 12

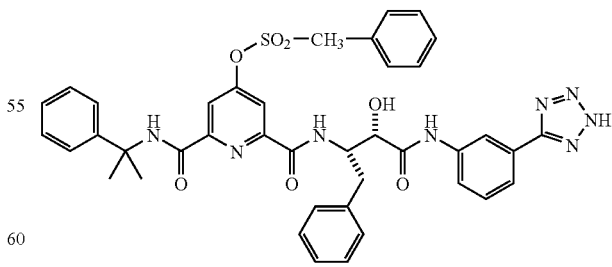

The object compound in a crude product was synthesized using compound of Reference example 12 and compound of Reference example 19 according to the procedure described in Example 1. The crude product was purified by preparative HPLC to give the object compound as a white powder.

Yield, 43%; purity, >98% by analytical HPLC (Rt, 28.25 min); TOF-MS m/z: 797.938 (M+Na)⁺.

Example 13

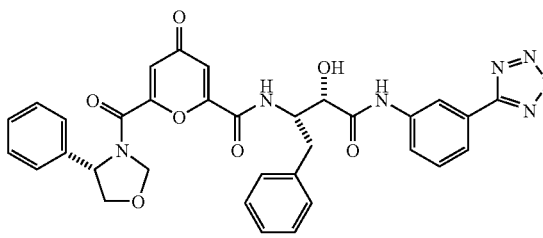

The object compound in a crude product was synthesized using compound of Reference example 14 and compound of Reference example 19 according to the procedure described in Example 1. The crude product was purified by preparative HPLC to give the object compound as a white powder.

Yield, 41%; purity, >98% by analytical HPLC (Rt, 21.76 min); TOF-MS m/z: 635.633 (M+H)⁺.

Example 14

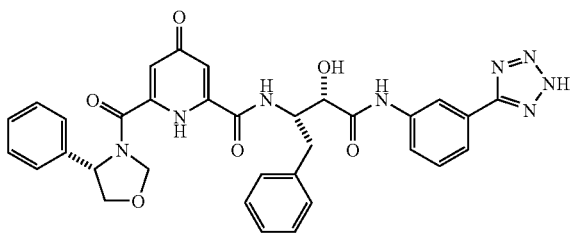

The object compound in a crude product was synthesized using compound of Reference example 15 and compound of Reference example 19 according to the procedure described in Example 1. The crude product was purified by preparative HPLC to give the object compound as a white powder.

Yield, 55%; purity, >98% by analytical HPLC (Rt, 22.10 min); TOF-MS m/z: 634.761 (M+H)⁺.

Example 15

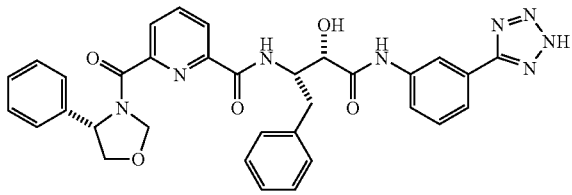

The object compound in a crude product was synthesized using compound of Reference example 16 and compound of Reference example 19 according to the procedure described in Example 1. The crude product was purified by preparative HPLC to give the object compound as a white powder.

Yield, 52%; purity, >98% by analytical HPLC (Rt, 22.89 min); TOF-MS m/z: 619.370 (M+H)⁺.

Example 16

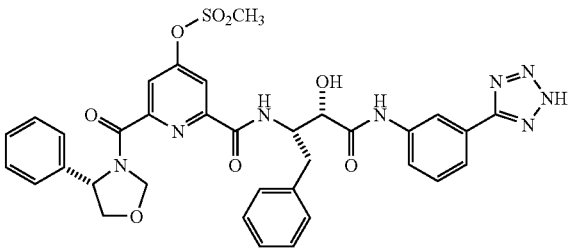

The object compound in a crude product was synthesized using compound of Reference example 17 and compound of Reference example 19 according to the procedure described in Example 1. The crude product was purified by preparative HPLC to give the object compound as a white powder.

Yield, 45%; purity, >98% by analytical HPLC (Rt, 23.22 min); TOF-MS m/z: 713.431 (M+H)⁺.

Example 17

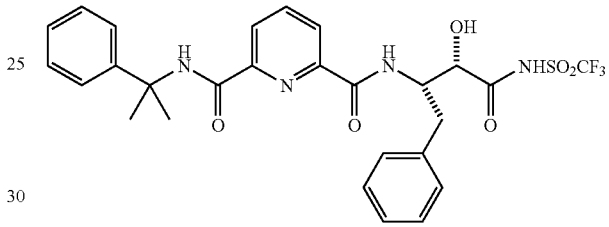

Compound of Reference example 10 (20 mg, 0.07 mmol) and compound of Reference example 22 (25 mg, 0.07 mmol) were dissolved in DMF, and thereto were added HOBT (10.7 mg, 0.07 mmol), triethyamine (9.7 μl, 0.07 mmol) and EDC.HCl (16 mg, 0.08 mmol), followed by stirring for 12 hours. After reaction, the reaction mixture was concentrated in vacuo. The residue was dissolved in ethyl acetate, washed with saturated brine, dried and then concentrated in vacuo. The crude product was purified by preparative HPLC to give the object compound as a white powder.

Yield, 43%; purity, >98% by analytical HPLC (Rt, 25.70 min); TOF-MS m/z: 615.649 (M+Na)⁺.

Reference Example 23

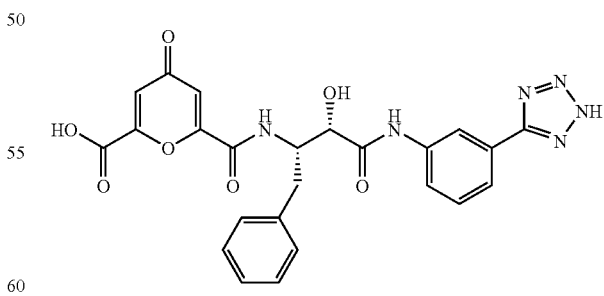

Compound of Reference example 19 (1.00 g, 2.67 mmol) was dissolved in DMF, and thereto were added TEA (1.12 mL, 8.00 mmol), chelidonic acid (447 mg, 2.43 mmol) and BOP (1.18 g, 2.67 mmol), followed by stirring at room temperature for 12 hours. The reaction mixture was concentrated in vacuo and then dissolved in ethyl acetate. The solution was washed with 10% citric acid, and saturated brine, sequentially. The organic layer was dried and then, concentrated in vacuo to give a crude product. The crude product was crystallized from n-hexane and dried to give the object compound as a white powder.

Yield, 99%; ESI-MS m/z: 503.31 (M−H)⁻.

Example 18

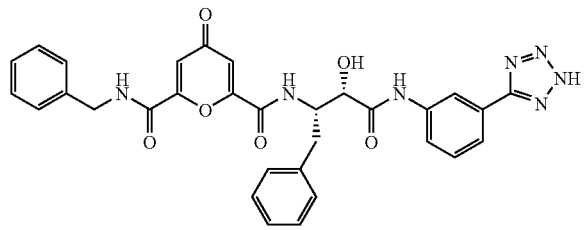 [SMILES: O=C(NCc1ccccc1)c1cc(=O)cc(C(=O)N[C@@H](Cc2ccccc2)[C@H](O)C(=O)Nc2cccc(-c3nn[nH]n3)c2)o1]

Compound of Reference example 23 (30 mg, 0.06 mmol) was dissolved in DMF, and thereto were added TEA (32 μl, 0.21 mmol), benzylamine (7.2 μl, 0.07 mmol) and BOP (32 mg, 0.07 mmol), followed by stirring at room temperature for 12 hours. The reaction mixture was concentrated in vacuo and then dissolved in ethyl acetate. The solution was washed with 10% citric acid and saturated brine sequentialy. The organic layer was dried and then, concentrated in vacuo. The crude product was purified by preparative HPLC to give the object compound as a white powder.

Yield, 85%; purity, >98% by analytical HPLC (Rt, 25.00 min); TOF-MS m/z: 594.46 (M+H)⁺.

Example 19

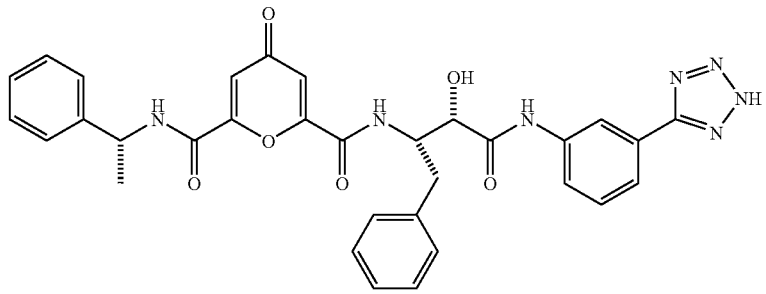 [SMILES: C[C@@H](NC(=O)c1cc(=O)cc(C(=O)N[C@@H](Cc2ccccc2)[C@H](O)C(=O)Nc2cccc(-c3nn[nH]n3)c2)o1)c1ccccc1]

The object compound in a crude product was synthesized using compound of Reference example 23 and (R)-phenethylamine according to the procedure described in Example 18. The crude product was purified by preparative HPLC to give the object compound as a white powder.

Yield, 2%; purity, >98% by analytical HPLC (Rt, 26.18 min); TOF-MS m/z: 608.760 (M+H)⁺.

Example 20

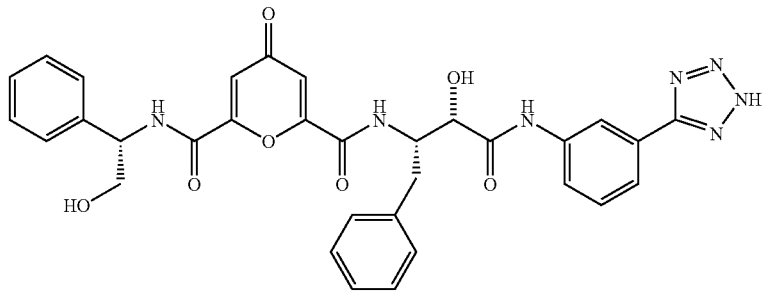 [SMILES: O=C(N[C@@H](Cc1ccccc1)[C@H](O)C(=O)Nc1cccc(-c2nn[nH]n2)c1)c1cc(=O)cc(C(=O)N[C@H](CO)c2ccccc2)o1]

The object compound in a crude product was synthesized using compound of Reference example 23 and L-phenylglycinol according to the procedure described in Example 18. The crude product was purified by preparative HPLC to give the object compound as a white powder.

Yield, quantitative; purity, >98% by analytical HPLC (Rt, 23.87 min); TOF-MS m/z: 624.460 (M+H)⁺.

Example 21

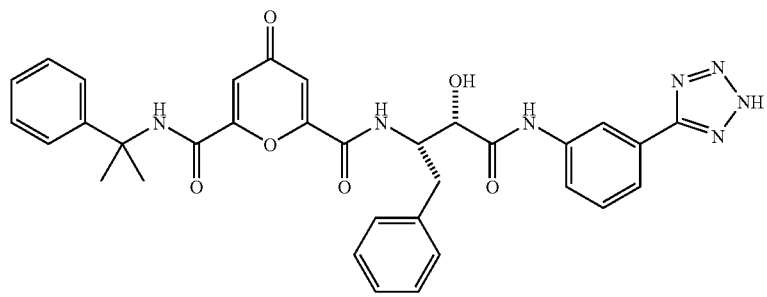 [SMILES: CC(C)(NC(=O)c1cc(=O)cc(C(=O)N[C@@H](Cc2ccccc2)[C@H](O)C(=O)Nc2cccc(-c3nn[nH]n3)c2)o1)c1ccccc1]

The object compound in a crude product was synthesized using compound of Reference example 23 and cumylamine according to the procedure described in Example 18. The crude product was purified by preparative HPLC to give the object compound as a white powder.
Yield, 95%; purity, >98% by analytical HPLC (Rt, 26.63 min); TOF-MS m/z: 644.11 (M+Na)$^+$.

Example 22

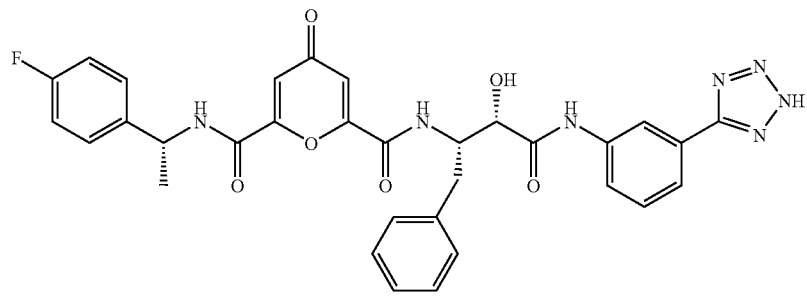 [SMILES: C[C@@H](NC(=O)c1cc(=O)cc(C(=O)N[C@@H](Cc2ccccc2)[C@H](O)C(=O)Nc2cccc(-c3nn[nH]n3)c2)o1)c1ccc(F)cc1]

The object compound in a crude product was synthesized using compound of Reference example 23 and (R)-1-(4-fluorophenyl)ethylamine according to the procedure described in Example 18. The crude product was purified by preparative HPLC to give the object compound as a white powder.
Yield, quantitative; purity, >98% by analytical HPLC (Rt, 27.24 min); TOF-MS m/z: 626.74 (M+H)$^+$.

The object compound in a crude product was synthesized using compound of Reference example 23 and (R)-1-(3-fuoruorophenyl)ethylamine according to the procedure described in Example 18. The crude product was purified by preparative HPLC to give the object compound as a white powder.
Yield, quantitative; purity, >98% by analytical HPLC (Rt, 26.38 min); TOF-MS m/z: 626.44 (M+H)$^+$.

Example 23

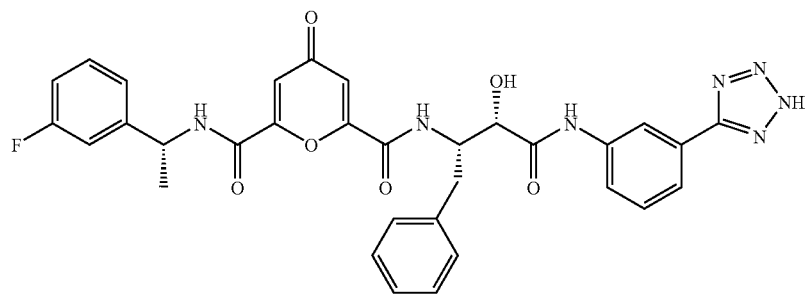 [SMILES: C[C@@H](NC(=O)c1cc(=O)cc(C(=O)N[C@@H](Cc2ccccc2)[C@H](O)C(=O)Nc2cccc(-c3nn[nH]n3)c2)o1)c1cccc(F)c1]

Example 24

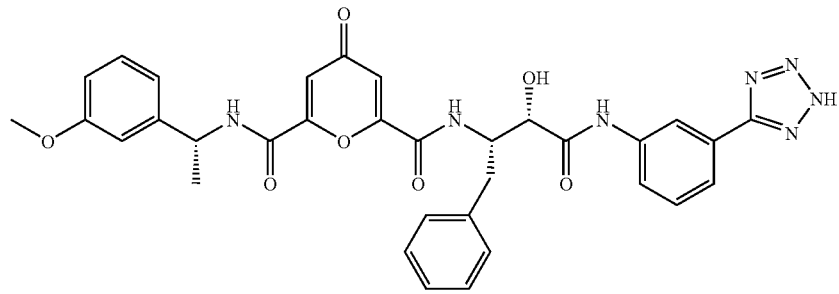 [SMILES: COc1cccc([C@@H](C)NC(=O)c2cc(=O)cc(C(=O)N[C@@H](Cc3ccccc3)[C@H](O)C(=O)Nc3cccc(-c4nn[nH]n4)c3)o2)c1]

The object compound in a crude product was synthesized using compound of Reference example 23 and (R)-1-(3-methoxyphenyl)ethylamine according to the procedure described in Example 18. The crude product was purified by preparative HPLC to give the object compound as a white powder.

Yield, 99%; purity, >98% by analytical HPLC (Rt, 26.23 min); TOF-MS m/z: 638.46 (M+H)$^+$.

Example 25

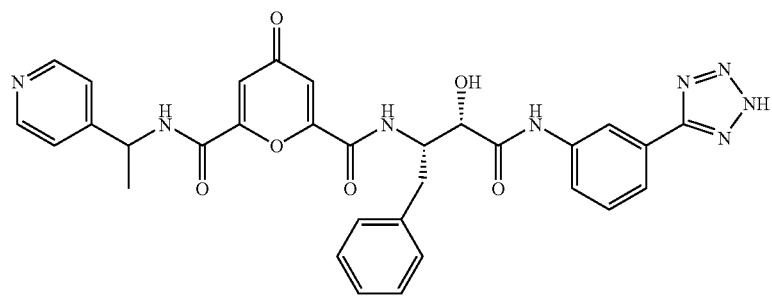 [SMILES: CC(NC(=O)c1cc(=O)cc(C(=O)N[C@@H](Cc2ccccc2)[C@H](O)C(=O)Nc2cccc(-c3nn[nH]n3)c2)o1)c1ccncc1]

The object compound in a crude product was synthesized using compound of Reference example 23 and 1-pyridinyl-ethylamine according to the procedure described in Example 18. The crude product was purified by preparative HPLC to give the object compound as a white powder.

Yield, quantitative; purity, >98% by analytical HPLC (Rt, 19.75, 19.88 min); TOF-MS m/z: 609.51 (M+H)$^+$.

Reference Example 24

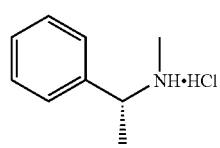

(R)-1-Phenylethyamine (121 mg, 1.00 mmol) was dissolved in THF-water (1:1) and thereto was added (Boc)$_2$O (222 mg, 1.02 mmol), followed by reacting at room temperature for 12 hours. After reaction, the reaction mixture was concentrated in vacuo, extracted with ethyl acetate, and washed with 10% citric acid and saturated brine. The organic layer was dried and then concentrated in vacuo to give the residue. The residue was crystallized from water and filtered off. The crystals were fully dried, dissolved in dried THF, and thereto was added sodium hydride (49 mg, 2.04 mmol). After 30 minutes methyl iodide (66 μl 1.06 mmol) was added, followed by reacting for 20 hours. The reaction mixture was concentrated in vacuo, and thereto was added water in an ice bath. The reaction mixture was extracted with ethyl acetate, washed with 10% citric acid and saturated brine. The organic layer was dried and concentrated in vacuo. To the residue was added anisole (0.88 ml, 8.18 mmol) and the mixture was dissolved in 4N hydrochloric acid/dioxane, followed by stirring 1 hour. The reaction mixture was concentrated in vacuo and recrystallized from ether to give the object compound as a white powder.

Yield, 78%; EI-MS m/z: 136.18 (M+H)$^+$.

Reference Example 25

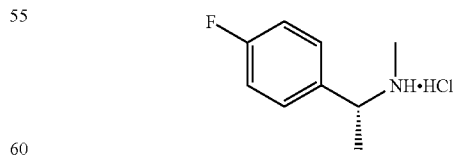

The object compound in a crude product as a white powder was synthesized using (R)-1-(4-fluorophenyl)ethylamine according to the procedure described in Example 24.

Yield, 70%; EI-MS m/z: 153.78 (M+H)$^+$.

Example 26

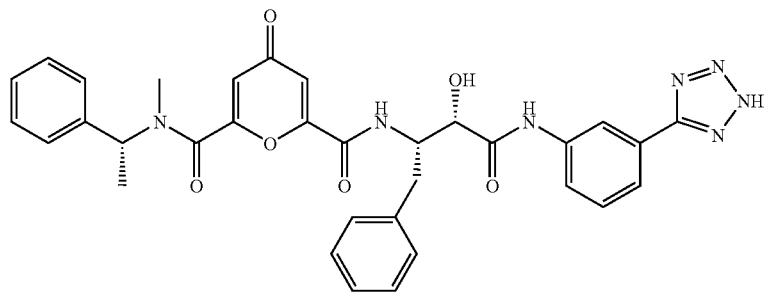 [SMILES: C[C@H](c1ccccc1)N(C)C(=O)c1cc(=O)cc(C(=O)N[C@@H](Cc2ccccc2)[C@H](O)C(=O)Nc2cccc(-c3nn[nH]n3)c2)o1]

The object compound in a crude product was synthesized using compound of Reference example 23 and compound of Reference example 24 according to the procedure described in Example 18. The crude product was purified by preparative HPLC to give the object compound as a white powder.

Yield, quantitative; purity, >98% by analytical HPLC (Rt, 26.52 min); TOF-MS m/z: 622.62 (M+H)$^+$.

Example 27

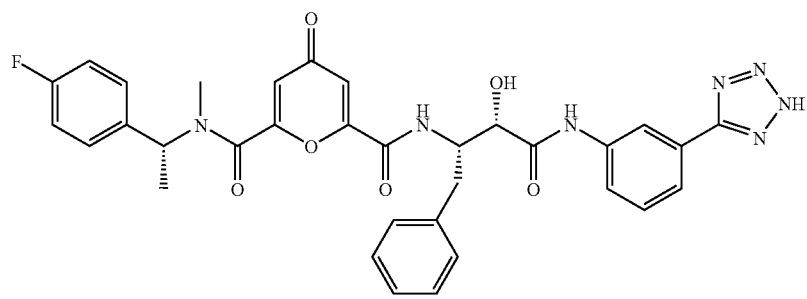 [SMILES: C[C@H](c1ccc(F)cc1)N(C)C(=O)c1cc(=O)cc(C(=O)N[C@@H](Cc2ccccc2)[C@H](O)C(=O)Nc2cccc(-c3nn[nH]n3)c2)o1]

The object compound in a crude product was synthesized using compound of Reference example 23 and compound of Reference example 25 according to the procedure described in Example 18. The crude product was purified by preparative HPLC to give the object compound as a white powder.

Yield, quantitative; purity, >98% by analytical HPLC (Rt, 27.32 min); TOF-MS m/z: 640.66 (M+H)$^+$.

Experiment Regarding Measurement of BACE1 Inhibitory Activity
Enzyme Used in Measurement As an enzyme having β-secretase activity, recombinant human BACE-1 (rhBACE-1) purchased from R&D systems (Minneapolis, Minn.) was used. rhBACE-1 is expressed as only an extracellular region (amino acid 1-460 residues) of recombinant human β-secretase, with a His tag at its carboxyl terminus in murine myeloma cell line, NS0. Purified secreted rhBACE1 is a mixture of a pro entity (about 75 kDa) and a mature entity (about 72 kDa). The purity is >90% (as determined by SDS-PAGE and visualized by silver stain), and enzyme activity is exhibited under weak acidity (pH 3.5-5.5).

Assessment of Enzyme Inhibitory Activity

Enzyme inhibitory activity of an inhibitor was assessed by quantitating an N-terminal fragment produced after cleaving the substrate with BACE1 by reverse HPLC using (7-methoxycoumarin-4-yl)acetyl-Ser-Glu-Val-Asn-Leu-Asp-Ala-Glu-Phe-Arg-Lys(2,4-dinitrophenyl)-Arg-Arg-NH$_2$ purchased from Peptide Institute (Osaka, Japan) as a substrate for BACE1. To 40 μL of 62.5 mM 2-(N-morpholino)ethansulfonic acid (MES)-CH$_3$COOH—NaOH buffer (pH 5.0), were added 1 μL of a solution of an inhibitor diluted with DMSO (100 μM), 4 μL of rhBACE-1 (6.25 ng/μL), and 5 μL of an aqueous solution (50% DMSO) of 250 μM substrate (7-methoxycoumarin-4-yl)acetyl-Ser-Glu-Val-Asn-Leu-Asp-Ala-Glu-Phe-Arg-Lys(2,4-dinitrophenyl)-Arg-Arg-NH$_2$ to initiate an enzyme reaction. After incubation at 37° C. for 60 minutes, 20 μL of 20% trichloroacetic acid was added to stop the reaction. And, inhibition % was calculated by measuring a fluorescent intensity of the N-terminal fragment (Ex, 328 nm; Em, 393 nm) using reverse phase HPLC (linear gradient of MeCN in aqueous TFA; flow rate, 1.0 mL/min).

The results are shown below.

TABLE 1

| Example Number | Inhibitory rate (%) (2 μM) |
|---|---|
| 1 | 70.1 |
| 2 | 28.8 |
| 3 | 26.8 |
| 5 | 70.4 |
| 6 | 66.9 |
| 7 | 50.8 |
| 8 | 65.1 |
| 9 | 65.6 |
| 10 | 69.1 |
| 11 | 83.6 |
| 12 | 33.6 |
| 13 | 95.6 |
| 14 | 82.7 |
| 15 | 92.6 |
| 16 | 95.6 |
| 17 | 37.4 |
| 21 | 80.8 |
| 22 | 75.8 |

The invention claimed is:

1. A compound represented by the following formula (1):

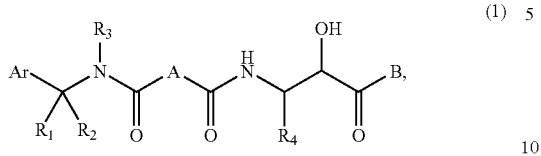

wherein Ar is a substituted or unsubstituted 5 to 6 membered mono cyclic aromatic group, and said aromatic group may have a hetero atom selected from nitrogen atom, oxygen atom and sulfur atom; $R_1$, $R_2$ and $R_3$ are hydrogen atom, substituted or unsubstituted alkyl group, substituted or unsubstituted allyl group, or substituted or unsubstituted aryl group, nitro group, halogen atom, cyano group, hydroxy group, or carboxy group, and $R_2$ and $R_3$ may be taken together with the adjacent nitrogen atom and carbon atom respectively to form a 3 to 6 membered ring which may be interrupted by oxygen atom, sulfur atom or substituted or unsubstituted amino group; $R_4$ is $C_{1-6}$ alkyl group, $C_{2-6}$ alkenyl group, $C_{2-6}$ alkinyl group, $C_{3-7}$ cycloalkyl group, phenyl group, $C_{1-6}$ alkyl group substituted by phenyl, phenylthio or a hetero ring provided that said phenyl, said phenylthio and said hetero ring may be substituted by $C_{1-6}$ alkyl, hydroxy, nitro, halogen, —$SO_3H$ or —$PO_4H$;

A is represented by the formula:

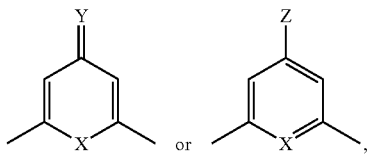

wherein X and Y are oxygen atom, NH or sulfur atom, Z is hydrogen atom, hydroxy group, amino group, or thiol group, and when Z is hydroxy group, amino group or thiol group, said group may be substituted by substituted or unsubstituted alkyl group, substituted or unsubstituted allyl group, or substituted or unsubstituted aryl group, substituted or unsubstituted acyl group, substituted or unsubstituted alkylsulfonyl group, substituted or unsubstituted arylsulfonyl group, or substituted or unsubstituted allylsulfonyl group; and B is hydroxy group, substituted or unsubstituted amino group, substituted or unsubstituted hydrazino group, substituted or unsubstituted hydroxyamino group, or substituted or unsubstituted aliphatic or aromatic amino group, or its pharmaceutically acceptable salt.

2. The compound according to claim 1 wherein in the generic formula (1) Ar is a substituted or unsubstituted phenyl group, $R_1$, $R_2$ and $R_3$ are hydrogen atom, substituted or unsubstituted alkyl group, and $R_2$ and $R_3$ may be taken together with the adjacent nitrogen atom and carbon atom respectively to form a 3 to 6 membered ring which may be interrupted by oxygen atom, sulfur atom or substituted or unsubstituted amino group; and B is hydroxy group, substituted or unsubstituted amino group, or the following formula:

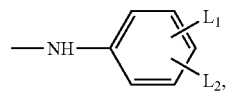

wherein $L_1$ and $L_2$ are hydrogen atom, substituted or unsubstituted alkyl group, substituted or unsubstituted allyl, substituted or unsubstituted aryl, nitro group, halogen atom, cyano group, hydroxy group, carboxy group, or a group selected from the following groups:

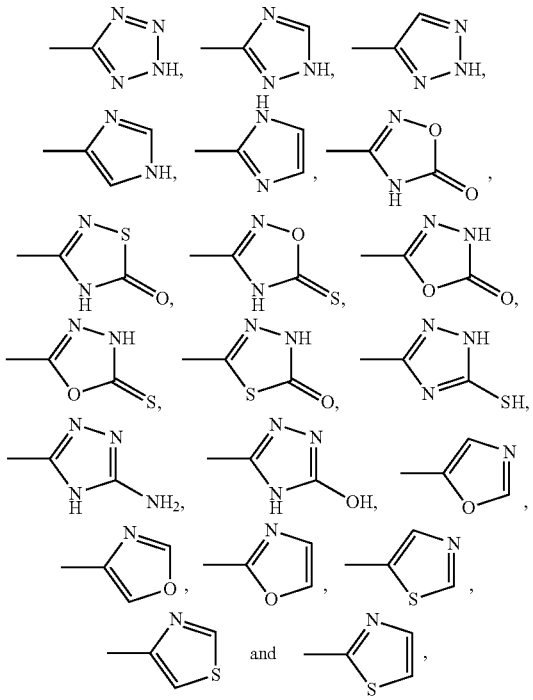

or its pharmaceutically acceptable salt.

3. The compound according to claim 1 wherein $R_4$ of the generic formula (1) is a group selected from following groups:

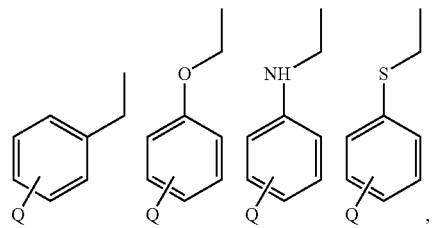

wherein Q is hydrogen atom, $C_{1-6}$ alkyl group, hydroxy group, nitro group, halogen atom, —$SO_3H$ or —$PO_4H$, or its pharmaceutically acceptable salt.

4. A pharmaceutical preparation containing a compound according to claim 1, or its pharmaceutically acceptable salt, as an active ingredient, and a pharmaceutically acceptable excipient or additive.

* * * * *